(12) United States Patent
Strayer et al.

(10) Patent No.: US 11,679,029 B2
(45) Date of Patent: Jun. 20, 2023

(54) ELECTRONIC GUILLOTINE VITRECTOMY CUTTER

(71) Applicant: JOHNSON & JOHNSON SURGICAL VISION, INC., Santa Ana, CA (US)

(72) Inventors: Scott G. Strayer, Rancho Santa Margarita, CA (US); Lauren M. Hickey, Los Angeles, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 163 days.

(21) Appl. No.: 17/131,603

(22) Filed: Dec. 22, 2020

(65) Prior Publication Data

US 2021/0161709 A1    Jun. 3, 2021

Related U.S. Application Data

(62) Division of application No. 15/725,182, filed on Oct. 4, 2017, now Pat. No. 10,874,549.

(51) Int. Cl.
| | | |
|---|---|---|
| *A61F 9/007* | (2006.01) | |
| *A61B 17/32* | (2006.01) | |
| *A61B 34/00* | (2016.01) | |
| *A61B 17/00* | (2006.01) | |
| *A61F 9/013* | (2006.01) | |
| *A61F 9/00* | (2006.01) | |

(52) U.S. Cl.
CPC .......... *A61F 9/00736* (2013.01); *A61B 17/32* (2013.01); *A61B 34/25* (2016.02); *A61F 9/00763* (2013.01); *A61B 2017/00017* (2013.01); *A61B 2017/00544* (2013.01); *A61F 9/0017* (2013.01); *A61F 9/013* (2013.01)

(58) Field of Classification Search
CPC .............. A61F 9/00736; A61F 9/00763; A61F 9/0017; A61F 9/013; A61B 17/32; A61B 34/25; A61B 2017/00017; A61B 2017/00544
See application file for complete search history.

(56) References Cited

U.S. PATENT DOCUMENTS

| | | |
|---|---|---|
| 4,428,748 A | 1/1984 | Peyman et al. |
| 4,555,645 A | 11/1985 | Atkinson |
| 4,940,468 A | 7/1990 | Petillo |
| 5,275,607 A | 1/1994 | Lo et al. |
| 5,716,363 A | 2/1998 | Josephberg |
| 6,043,623 A | 3/2000 | McCary |
| 6,106,491 A | 8/2000 | Gianutsos |
| 9,358,103 B1 * | 6/2016 | Wortz ................... A61F 2/1694 |
| 9,486,360 B2 | 11/2016 | Chon et al. |
| 2005/0287007 A1 | 12/2005 | Leonhard |

(Continued)

FOREIGN PATENT DOCUMENTS

| | | |
|---|---|---|
| EP | 3212139 B1 | 11/2018 |
| WO | 0241788 A1 | 5/2002 |

*Primary Examiner* — Phong Son H Dang
(74) *Attorney, Agent, or Firm* — Johnson & Johnson Surgical Vision, Inc.

(57) ABSTRACT

A vitrectomy apparatus is provided, including a disposable cutter that incorporates a linear voice coil motor to generate consistent and rapid guillotine action without the use of a rotary motor or traditional linear motor. The apparatus includes voice coil actuator to provide for a forward and backward reciprocating motion cutting blade.

11 Claims, 7 Drawing Sheets

(56) References Cited

U.S. PATENT DOCUMENTS

| | | |
|---|---|---|
| 2008/0052269 A1 | 2/2008 | Abdo et al. |
| 2008/0188881 A1 | 8/2008 | Chon |
| 2008/0208233 A1 | 8/2008 | Barnes et al. |
| 2011/0118729 A1 | 5/2011 | Heeren et al. |
| 2011/0295296 A1 | 12/2011 | Charles |
| 2012/0310146 A1* | 12/2012 | Easley ............... A61F 9/00736 604/22 |
| 2013/0144317 A1 | 6/2013 | Valencia |
| 2013/0178933 A1* | 7/2013 | Serrano Olmedo ...... A61F 2/14 623/4.1 |
| 2015/0157503 A1* | 6/2015 | Chon .................. A61F 9/00763 606/169 |
| 2017/0328896 A1 | 11/2017 | Luloh et al. |
| 2018/0243134 A1 | 8/2018 | Dean et al. |
| 2018/0318132 A1 | 11/2018 | Clauson et al. |
| 2018/0369016 A1 | 12/2018 | Underwood |

\* cited by examiner

ELECTRONIC GUILLOTINE VITRECTOMY CUTTER

CROSS-REFERENCE TO RELATED APPLICATIONS

This application is a divisional of and claims priority to U.S. patent application Ser. No. 15/725,182, filed Oct. 4, 2017, which is incorporated herein by reference in its entirety.

FIELD OF THE INVENTION

The present invention relates generally to the field of surgical hand pieces, and, more specifically, to vitrectomy surgical hand pieces for ocular surgical procedures.

BACKGROUND

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or hand piece, through the corneal incision. The hand piece includes a needle which is ultrasonically driven once placed within the incision to emulsify the eye lens, or to break the cataract into small pieces. The broken cataract pieces or emulsified eye lens may subsequently be removed using the same hand piece, or another hand piece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification hand piece, is critical to the procedure performed. Different medically recognized techniques have been utilized to control the fluid flow during the lens removal portion of the surgery. Among these, one popular technique is a simultaneous combination of phacoemulsification, irrigation and aspiration using a single hand piece. This method includes making the incision, inserting the handheld surgical implement to emulsify the cataract or eye lens, and, simultaneously with this emulsification, having the hand piece provide a fluid for irrigation of the emulsified lens using a sleeve that surrounds a needle and a vacuum for aspiration of the emulsified lens and inserted fluids.

Currently available phacoemulsification systems, such as those mentioned above, typically include a variable speed peristaltic pump and/or vacuum pump, a vacuum sensor, an adjustable source of ultrasonic power, and a programmable microprocessor with operator-selected presets for controlling aspiration rate, vacuum and ultrasonic power levels. The phacoemulsification hand piece is interconnected with a control console by an electric cable for powering and controlling a piezoelectric transducer that drives the action of the hand piece. Tubing provides irrigation fluid to the eye through the hand piece and enables withdrawal of aspiration fluid from an eye through the hand piece.

Generally, irrigation and aspiration are employed by the surgeon using the device to remove unwanted tissue and maintain pressure within the eye. Moreover, the use of, and particularly the pressurization of, the irrigation fluid is critical and may, for example, prevent the collapse of the eye during the removal of the emulsified lens. Irrigation fluid pressure is also used to protect the eye from the heat generated by the ultrasonic cutting needle and may suspend fragments created during the surgery in fluid for more easy removal through aspiration.

Current phacoemulsification systems use either an electronic rotary vitrectomy cutter or a pneumatic driven vitrectomy cutter. Existing electronic rotary vitrectomy cutters use an oscillating cutting action which can result in an incomplete cut. This incomplete cut can pull vitreous material rather than cutting it. While a pneumatic vitrectomy requires a significant amount of hardware components, both in terms of cost and space, along with complex algorithms to ensure the system is providing sufficient pneumatic pressure to complete a cut.

Based on the foregoing, it would be advantageous to provide a system that enables the combination of an electronic rotary vitrectomy cutter drive with the mechanical action of a pneumatic cutter.

BRIEF SUMMARY OF THE INVENTION

By combining the drive of a rotary vitrectomy cutter with the mechanical action of a pneumatic cutter, the development of a disposable cutter that enables a build at lower cost, is smaller, and is simpler is realized. The cutter incorporates a Linear Voice Coil Motor (LVCM) into the design to generate consistent and rapid guillotine action in a smaller design without the use of a rotary motor or the size of a linear motor.

The present invention comprises a vitrectomy apparatus, further comprising a vitrectomy hand piece comprising a guillotine cutting device comprising a bobbin (which may be wound with magnet wire), creating a coil that when a current is run through it creates an electromagnet, permanently fixed to an internal cutting shaft, a magnet permanently (for example, a ring shaped magnet) affixed to the internal center of a shell composed of ferrous materials of the guillotine cutting device, and a controller configured to control operation of the internal cutting shaft, wherein the controller is configured to control motion of the bobbin in response to an application of voltage causing the internal cutting shaft to move forward and backwards with difference in polarity of the permanently fixed magnet. The vitrectomy apparatus may also comprise a tube with at least one first opening at the distal end of the hand piece communicatively connected to at least one second opening at the proximal end to allow for aspirated fluid to exit from the apparatus.

The present invention comprises a method of controlling a guillotine cutting device by providing a bobbin wound with one or more pieces of magnetic wiring and permanently affixed to an internal cutting shaft, the one or more pieces of magnetic wiring capable of generating a magnetic field, providing at least one magnet affixed to the internal center of a shell of the guillotine cutting device, and generating at least one magnetic field from a provided voltage, wherein the bobbin moves forward and backward based on a difference in polarity of the magnet in response to the magnetic field. The magnet core of the present invention may be permanently affixed to the internal cutting shaft. The present invention may provide voltage that is pulsed and may be between 1 and 24 volts and the voltage may control the speed of the bobbin movement. The present invention may also include at least one heat sink.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

Figure 1:
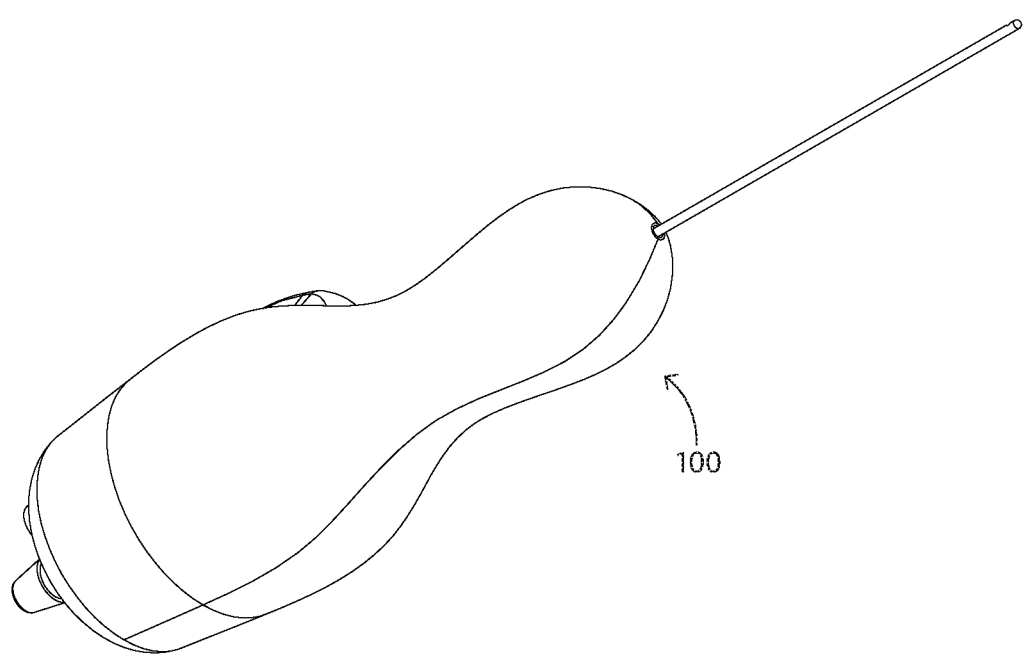
FIG. 1 illustrates a prospective view of an embodiment of the present invention.
Figure 2A:
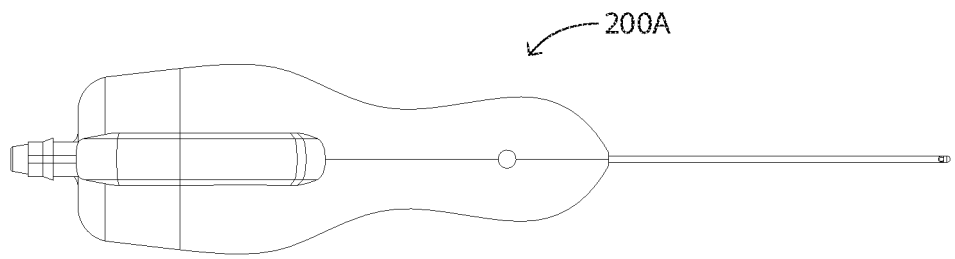
FIG. 2A illustrates a top view of the surgical device.
Figure 2B:
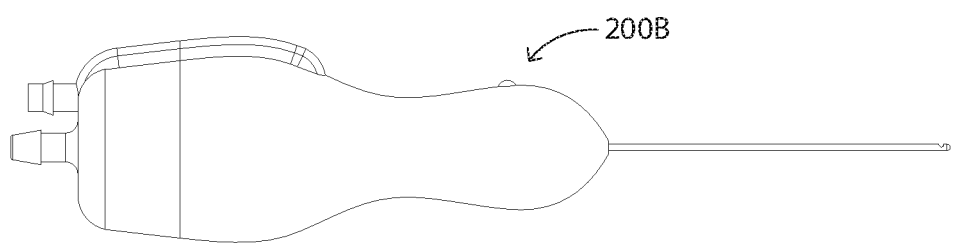
FIG. 2B illustrates a side view of the surgical device.
Figure 2C:
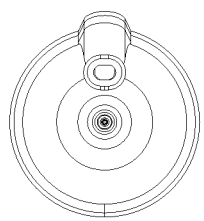
FIG. 2C illustrates a rear view of the surgical device.
Figure 2D:
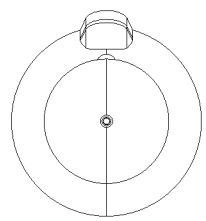
FIG. 2D illustrates a front view of the surgical device.
Figure 2E:
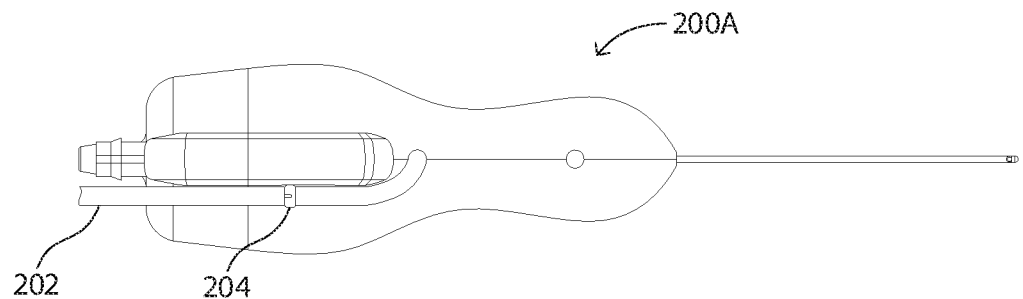
FIG. 2E illustrates a top view of the surgical device.
Figure 2F:
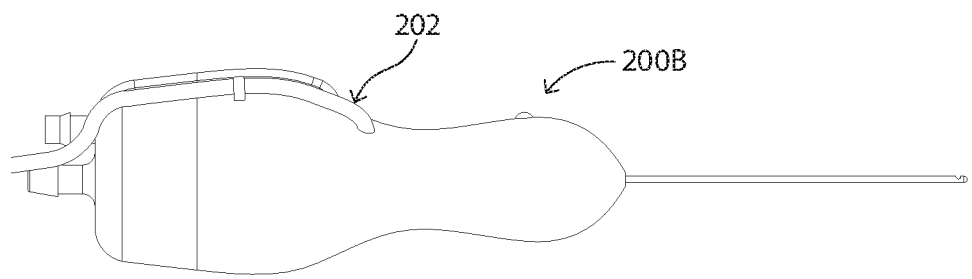
FIG. 2F illustrates a side view of the surgical device.
Figure 2G:
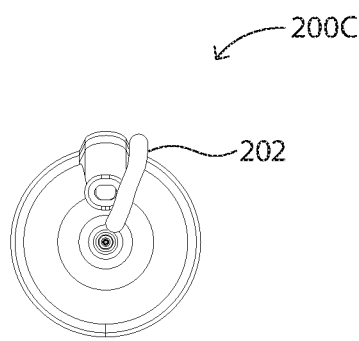
FIG. 2G illustrates a rear view of the surgical device.
Figure 2H:
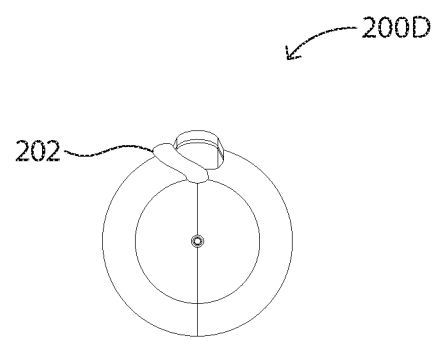
FIG. 2H illustrates a front view of the surgical device.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on," "engaged to," "connected to," or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer, or section without departing from the teachings of the exemplary embodiments.

The present design provides a system and method for a high-speed guillotine action vitrectomy cutter that may be used to precisely set and vary the cutting speed of the associated cutting blade mechanism over a wide range of operational speeds.

While the present design may be employed in various systems involving cutting blades, it is illustrated herein in an exemplary phacoemulsification-vitrectomy system. The present design is directed to accurate, reliable, and efficient use of a voice coil actuator to provide for a forward and backward reciprocating motion cutting blade in a vitrectomy handpiece used in a medical instrument system. The present design will be discussed herein with a particular emphasis on a medical or hospital environment, where a surgeon or health care practitioner performs. For example, an embodiment of the present invention is a phacoemulsification surgical system that comprises an integrated high-speed control module for the vitrectomy handpiece. The surgeon or practitioner may adjust or set the blade speed via a graphical user interface (GUI) module, a switch located on the handpiece, or a foot pedal switch to control the high-speed vitrectomy handpiece.

As illustrated in FIG. 1, the present invention may provide an ergonomic hand piece 100 which may be held easily by the fingers and/or hands of an operator and which may house a mechanism suitable to provide a vitrectomy cutting mechanism. The body of the surgical instrument may include texture on the exterior to aid with the actual gripping of the hand piece. As illustrated by the views 200A-200H presented in FIGS. 2A-2H, the hand piece body may contain at least one feature indicative of the location of the cutter opening of the surgical instrument to provide a tactile indicator to the user of the device as to the orientation of the hand piece. Such a feature may include a detent, a raised portion, or a combination thereof, for example. In at least one non-limiting embodiment, as illustrated in FIGS. 2E-2H, aspiration line 202 may be outside or externally located in relation to the body of the device to improve upon the strength of the device's drive mechanism. Aspiration line 202 may be fastened permanently or semi-permanently using fastener 204.

In an embodiment of the present invention, the surgical instrument may comprise a primary shaft extending out from the body of the hand piece which may further comprise at least one port and/or at least one cutting element. The primary shaft may also include at least one of an opening at the distal end for aspiration and at an opening at the proximal end for aspirated fluid and material to exit the at least one shaft portion of the surgical instrument. The primary shaft may be sheathed in an outer shaft which may be communicatively attached to the hand piece and may, for example, provide rigidity and/or guidance to the primary shaft.

The surgical instrument may contain a permanent magnet that is fixed substantially within the center of a shell. The shell, which may comprise soft iron, may preferably be of a steel composition or other ferrous materials. The permanent magnet may be affixed to the shell and may be in electromagnetic communication with at least one voice coil. Alternatively, the permanent magnet may be a ring-shaped magnet. The voice coil may be a single phase linear voice coil actuator, which may provide direct, cog-free linear motion that is substantially free of backlash, irregularity, and/or energy loss which may result from converting rotary to linear motion. The voice coil may also comprise a tubular coil of wire situated within a radially oriented magnetic field.

In an embodiment of the present invention, the linear voice coil motor may be composed of two parts, a cylinder composed of ferrous materials with a cylindrical magnet in the center (i.e., magnet core) and a wire wrapped bobbin which may be energized to create the opposing magnetic field which drives the motor. The linear voice coil may also be designed and oriented in two different directions. In at least one embodiment, a bobbin forward design may fix the magnet core in place and move the bobbin. In another embodiment, a magnet forward design may fix the bobbin in place. In yet another embodiment of the present invention, a permanent magnet may be affixed to the center of a bobbin and surrounded by an iron magnet housing. Alternatively, the hand piece housing may be composed entirely of magnetic materials rather than iron. The core of the magnet housing may therefore be an iron core or another permanent magnet at the center.

A gap may exist between the shell and the permanent magnet, the shell and the voice coil, and the voice coil and the permanent magnet. The gap may be filled with air, a gas, and/or fluid, such as aspirated fluid from the surgical site as will be discussed herein. The air and/or fluid in the gap provides freedom of movement of the voice coil and may provide cooling of the voice coil and surrounding components. In an embodiment of the present invention, the axial length of the coil may exceed that of the magnet by the amount of coil travel which may provide a superior force-to-power ratio and allow for greater heat dissipation.

Figure 3A:
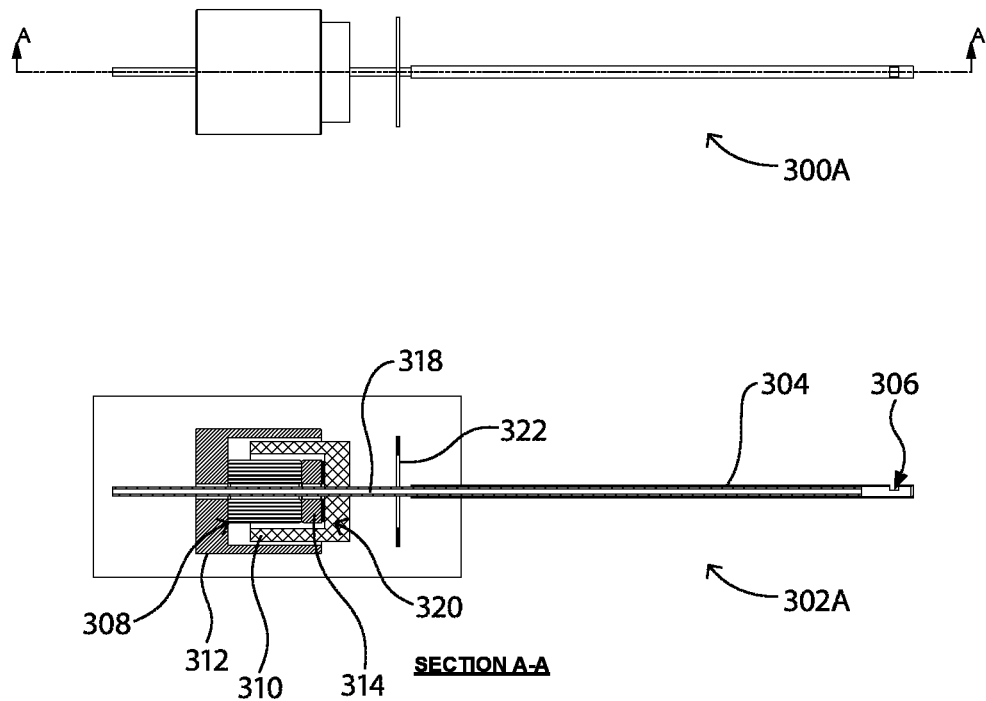
FIG. 3A illustrates a cross-sectional view of the surgical device in an opened state.
Figure 3B:
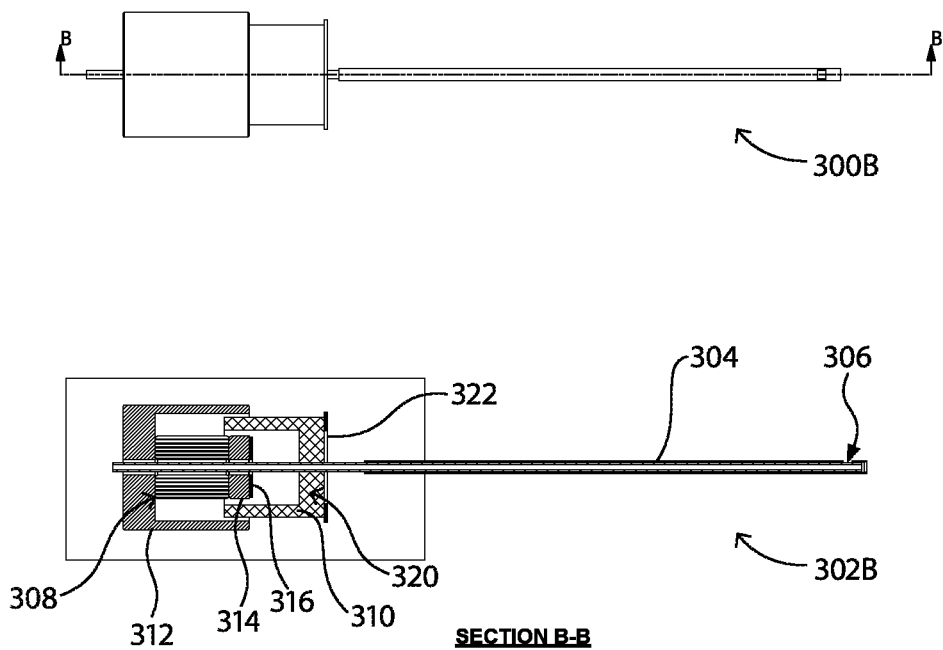
FIG. 3B illustrates a cross-sectional view of the surgical device in a closed state.

As illustrated in FIGS. 3A and 3B, cross-sectional views illustrating an electronic guillotine vitrectomy cutting system within a surgical hand piece illustrate the guillotine cutting mechanism in the "open" or "backward" position, and in the "closed" or "forward" position, respectively. As illustrated in FIGS. 3A and 3B, the at least one permanent or solid magnet 308 may be affixed to a magnet housing, such as shell 312, at the distal end and may have at its proximate end an assembly comprising a solid magnet cap 314 and a dampening material 316 (for example for minimizing or eliminating vibration and/or sound). The cap may be comprised of ferrous materials and have a high iron count. Even further, cap 314 may include a sharp corner on the end face nearest to the shell at the most distal end. Similarly, the distal end of the shell 312 closest to the cap 314 may also have a substantially sharp and/or squared corner which, when taken together with the shape of the cap, may enhance the magnetic field density which may act on the voice coil. Dampening material 316 may be silicone, rubber, or other foam-type vibration dampening or dissipating material and/or may be a spring or spring-like device.

The voice coil 310 may be wrapped in motor winding wire of either a round or flattened profile wrapped around a bobbin. The bobbin may be composed of plastic, metal, rubber, or a combination thereof. The bobbin windings may be electrically connected to a system and the bobbin may be permanently fixed to the internal shaft 318. Internal shaft 318 may extend axially through the body of the surgical instrument and coaxially through external shaft 304. Voice coil 310 may similarly comprise substantially sharp and/or squared corners 320 which, when taken together with the shape of the cap 314 and shell 312, may enhance the magnetic field density which may act on the voice coil.

In at least one embodiment of the surgical instrument, during operation, the distal end of the external shaft 304 may contact the interior of a patient's eye. Shaft 318 may be permanently affixed to coil 310. The internal shaft 304 may include opening 306 in the sidewall near the distal end of internal shaft 318. The opening 306 may comprise a port allowing for an aspiration path into the patient's eye and may further comprise at least one surface suitable for providing a cutting action, such as a blade portion.

In an embodiment of the invention, a drive voltage (between 1-24 Volts, preferably 1-5 Volts) may cause the voice coil 310 to move in a back and forth motion in response to differences in polarity of the drive voltage. The bobbin motion may or may not be constrained axially within the body of the surgical instrument. When the voltage differential applied to the bobbin windings is zero, no magnetic field is generated by the bobbin windings. When the voltage differential is greater than zero, a magnetic field is generated causing a magnetic polarity opposite of the fixed magnet 308 which in turn causes the bobbin to move forward and extend the internal shaft 318. When the voltage differential is zero, no magnetic field is generated; causing the bobbin to move backward towards the fixed magnet 308 and the internal shaft 318 is retracted. As the voice coil 310 moves in the back and forth motion, it may be bounded by either silicone, rubber, or other foam-type vibration dampening or dissipating material. In an embodiment, the voice coil may be bounded by a hard material, including, but not limited to, metal or plastic. A spring 316', as schematically represented in FIG. 3D, may also be included to stabilize or slow the bobbin speed as the bobbin moves from forward stroke to backward stroke. Such a stabilization or slowing process may reduce vibration of the surgical instrument.

As the internal shaft moves forward and backwards, it may pass through a seal at the front of the hand piece housing as well as a seal at the rear of the hand piece housing. The use of a front seal may ensure that near maximum vacuum is applied through the aspiration hole provided in the internal shaft and that the vacuum is not lost through the space between the exterior surface of the internal shaft and the interior of the exterior shaft. The seal at the back of the device may create an open space within the barbed fitting where a vacuum may be provided from an aspiration line from the surgical system (not shown). The rear seal may create the aforementioned vacuum which may be applied through the open end of the internal shaft which extends the vacuum to opening 306. The seals may be integrated with to the surgical instrument by over-molded rubber, silicone-type materials, or separate components, such as O-rings, canted coil spring seals, or separate molded components, for example.

The backward/forward motion of internal shaft 318 may be controlled by a magnetic field as previously described above. Dampening material 316 may be utilized to control forward and rear positioning of voice coil 310 in relation to permanent magnet 308. Consistent and rapid guillotine action is realized by the linear voice coil motor to produce the necessary cuts per minute for anterior vitrectomy operation.

Figure 3C:
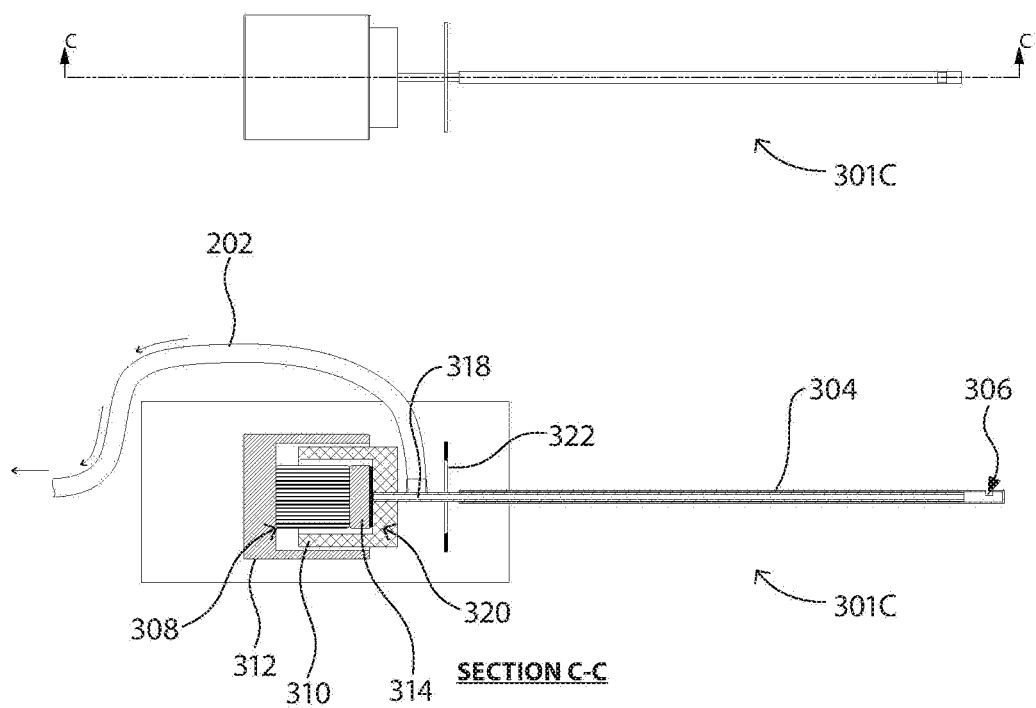
FIG. 3C illustrates a cross-sectional view of the surgical device in an opened state.
Figure 3D:
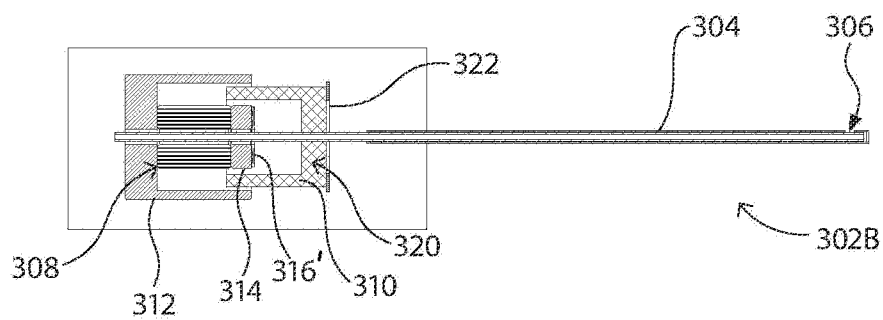
FIG. 3D illustrates a cross-sectional view of the surgical device similar to FIG. 3B shown in a closed state and with an optional spring.

In an embodiment of the present invention, as illustrated in FIG. 3C, aspiration line 202, may be communicatively connected to internal shaft 318. The aspiration line 202 may be positioned along the longitudinal axis of internal shaft 318 and may be positioned proximate to the intersection of the internal shaft 318 and voice coil 310. Such an arrangement may allow the internal shaft 318 to terminate in the voice coil 310 and not otherwise interfere with or penetrate the solid magnet assembly. In this embodiment of the present invention, the construction and performance of the solid magnet assembly may be simplified and improved by not necessitating, for example, the milling of a passage through the solid magnet. Aspiration line 202 may be affixed mechanically to internal shaft 318 and may comprise a flexible attachment means suitable to withstand the movement of internal shaft 318.

Figure 4A:
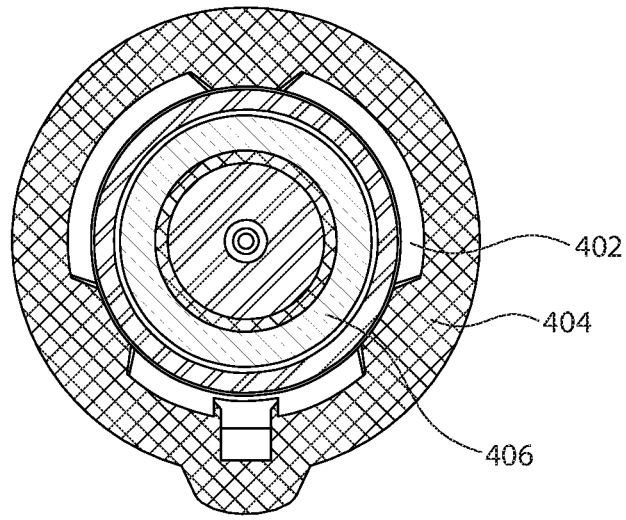
FIGS. 4A and 4B illustrate cross sectional views of embodiments of the present invention.
Figure 4B:
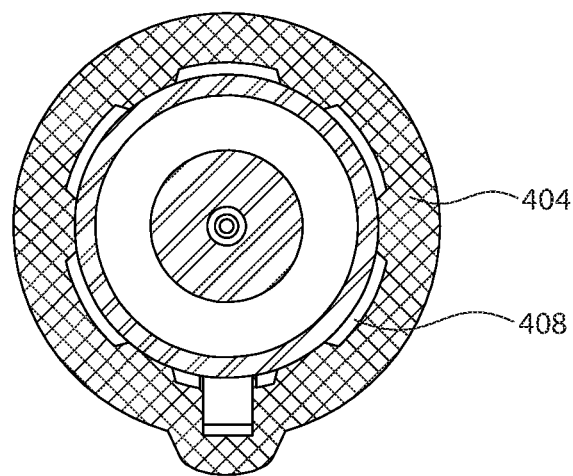

As illustrated in FIG. 4A, a cross section 400 taken towards the proximate end of the voice coil motor assembly illustrates guiding rails 402 in contact with shell assembly 404 for use in providing motion control over the voice coil 406. As illustrated, a set of three independent guide rails are shown. As would be understood by those skilled in the art, the number and size of rails may be varied depending on design requirements. Although the rails may take on various shapes, guiding rails 402 comprise angled and/or chamfered corners to minimize unwanted movement and/or vibrations. Similarly, as illustrated in cross section 410 of FIG. 4B taken near the distal end of the voice coil assembly, and at least partially independent plurality of guiding rails 408 may be provided to reduce movement and vibrations of the permanent affixed magnet relative to the shell assembly 404.

Figure 5A:
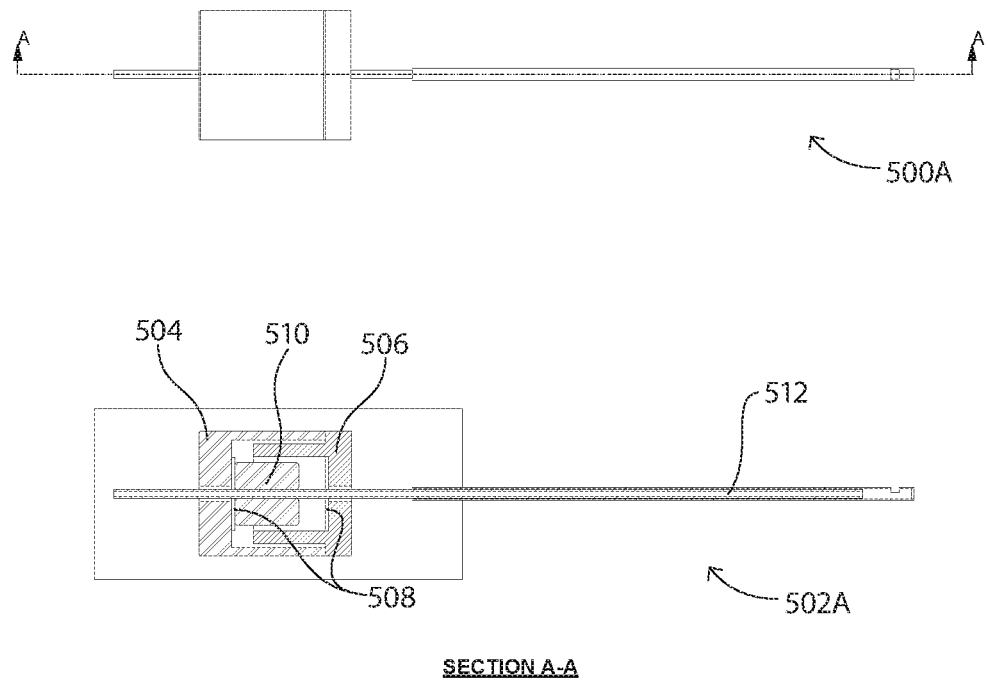
FIG. 5A illustrates a cross-sectional view of the surgical device in an opened state in at least one alternate embodiment.
Figure 5B:
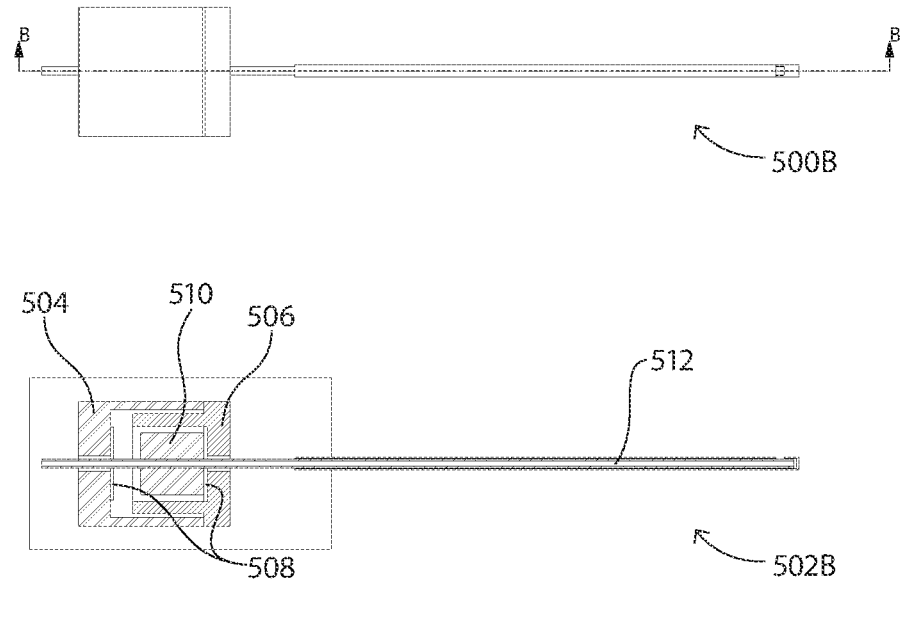
FIG. 5B illustrates a cross-sectional view of the surgical device in a closed state in at least one alternate embodiment.

As illustrated in FIGS. 5A and 5B, cross-sectional views 500A, 502A, 500B and 502B illustrate an alternative electronic guillotine vitrectomy cutting system in accordance with the disclosed invention. FIG. 5A shows the cutter in a backward position and FIG. 5B shows the cutter in a forward position. In the alternate embodiment, magnet housing or shell 504 and voice coil 506 may be permanently fixed to the internal shell. Magnet housing 504 may be comprised of ferrous materials. In this embodiment, magnet 510 would move back and forth in response to voltage application in the manner described herein. Moving magnet 510 may be affixed to cutting shaft 512 which is contained by the external shaft with opening. Dampening material 508 may be provided in the front and rear to reduce noise and/or vibration. In this embodiment, the moving mass is reduced which results in reduced vibration an improved thermal dissipation of the heat created by the coil. The fixed coil 506 may be equipped with a passive heat exchanger such as a heat sink.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. A method of controlling a guillotine cutting device, the device comprising:
   providing a bobbin wound with one or more pieces of magnetic wiring and affixed to an internal cutting shaft, the one or more pieces of magnetic wiring capable of generating a magnetic field;
   providing at least one magnet in communication with the bobbin; and
   generating at least one magnetic field from a provided voltage, wherein the bobbin moves forward and backward based on a difference in polarity of the magnet in response to the magnetic field, wherein at least one of a shape of the bobbin and a shape of the at least one magnet enhances the magnetic field density of the generated magnetic field.

2. The method of claim 1, wherein the at least one magnet is affixed to an internal center of a shell of the guillotine cutting device.

3. The method of claim 1, wherein the provided voltage is pulsed.

4. The method of claim 1, wherein the provided voltage is between 1 and 5 volts.

5. The method of claim 1, wherein the provided voltage controls the speed of the bobbin movement.

6. The method of claim 1, further comprising providing at least one heat sink.

7. The method of claim 1, wherein a bobbin motion is bounded by one or more dampening materials.

8. A method of controlling a guillotine cutting device, the device comprising:
   providing a bobbin wound with one or more pieces of magnetic wiring and affixed to an internal cutting shaft, the one or more pieces of magnetic wiring capable of generating a magnetic field;

providing at least one magnet in communication with the bobbin; and generating at least one magnetic field from a provided voltage, wherein the bobbin moves forward and backward based on a difference in polarity of the magnet in response to the magnetic field, wherein the provided voltage is between 1 and 24 volts.

9. A method of controlling a guillotine cutting device, the device comprising:

providing a bobbin wound with one or more pieces of magnetic wiring and affixed to an internal cutting shaft, the one or more pieces of magnetic wiring capable of generating a magnetic field;

providing at least one magnet in communication with the bobbin; and generating at least one magnetic field from a provided voltage, wherein the bobbin moves forward and backward based on a difference in polarity of the magnet in response to the magnetic field, wherein bobbin movement is bounded by one or more dampening materials comprising a spring.

10. A method of controlling a guillotine cutting device, the device comprising:

providing a bobbin wound with one or more pieces of magnetic wiring and affixed to an internal cutting shaft, the one or more pieces of magnetic wiring capable of generating a magnetic field;

providing at least one magnet in communication with the bobbin; and generating at least one magnetic field from a provided voltage, wherein the bobbin moves forward and backward based on a difference in polarity of the magnet in response to the magnetic field, wherein bobbin movement is bounded by one or more dampening materials fixed to the magnet.

11. The method of claim 10, wherein the one or more dampening materials comprise one or more of silicone, rubber, foam, metal, or plastic.

* * * * *